US009137990B2

(12) United States Patent
Seybold et al.

(10) Patent No.: US 9,137,990 B2
(45) Date of Patent: Sep. 22, 2015

(54) **METHODS OF MONITORING AND CONTROLLING THE WALNUT TWIG BEETLE, *PITYOPHTHORUS JUGLANDIS***

(75) Inventors: Steven J. Seybold, Davis, CA (US); Paul L. Dallara, Pleasanton, CA (US); Lori J. Nelson, Alameda, CA (US); Andrew D. Graves, Albuquerque, NM (US); Stacy M. Hishinuma, Burbank, CA (US); Regine Gries, Coquitlam (CA)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 357 days.

(21) Appl. No.: 13/548,319

(22) Filed: Jul. 13, 2012

(65) Prior Publication Data

US 2013/0014428 A1      Jan. 17, 2013

Related U.S. Application Data

(60) Provisional application No. 61/508,441, filed on Jul. 15, 2011.

(51) Int. Cl.
| | |
|---|---|
| *A01M 1/02* | (2006.01) |
| *A01P 17/00* | (2006.01) |
| *A01P 19/00* | (2006.01) |
| *A01N 31/02* | (2006.01) |
| *A01N 43/90* | (2006.01) |

(52) U.S. Cl.
CPC ............... *A01N 31/02* (2013.01); *A01N 43/90* (2013.01)

(58) Field of Classification Search
CPC ............................ A01N 49/00; A01M 1/106
See application file for complete search history.

(56) References Cited

U.S. PATENT DOCUMENTS

| | | | | |
|---|---|---|---|---|
| 4,205,084 | A | | 5/1980 | Vite |
| 4,839,383 | A | | 6/1989 | Vite |
| 4,994,268 | A | | 2/1991 | Weiser |
| 5,223,542 | A | | 6/1993 | Byers |
| 5,750,129 | A | * | 5/1998 | Wakarchuk ............... 424/408 |
| 6,051,612 | A | * | 4/2000 | Borden et al. ............ 514/693 |
| 6,217,891 | B1 | | 4/2001 | Borden |
| 6,479,046 | B2 | | 11/2002 | Dickens |
| 6,958,360 | B2 | | 10/2005 | Dickens |

OTHER PUBLICATIONS

Bartelt RJ, et al., "Male-produced aggregation pheromone of *Carpophilus sayi*, a nitidulid vector of oak wilt disease, and pheromonel comparison with *Carpophilus lugubris*," 2004 Agricultural and Forest Entomology 6:39-46.
Browne LE, et al., "An emergence cage and refrigerated collector for wood-boring insects and their associates," 1972 J. Econ. Entomol. 65: 1499-1501.
Cochran WG, "Sampling Techniques," 3rd edition,1977 New York: John Wiley & Sons.
Graves DA, et al., "Protection of spruce from colonization by the bark beetle, *Ips perturbatus*, in Alaska," 2008 Forest Ecology and Management 256:1825-1839.).
Kolařík M, et al., "*Geosmithia morbida* sp. nov., a new phytopathogenic species living in symbiosis with the walnut twig beetle (*Pityophthorus juglandis*) on Juglans in USA," 2011 Mycologia 103: 325-332.).
Seybold SJ, et al. "Recent collecting reveals new state records and the extremes in the distribution of the walnut twig beetle, *Pityophthorus juglandis* Blackman (Coleoptera: Scolytidae), in the United States," 2012 Pan-Pacific Entomol 88 (2): 277-280.
Seybold SJ, et al. "Quick guide: Installing, maintaining, and servicing walnut twig beetle pheromone-baited traps, University of California Agriculture and Natural Resources, Statewide Integrated Pest Management Program," Apr. 2012, pp. 1-2.
Seybold SJ, et al., "Detecting and Identifying the Walnut Twig Beetle: Monitoring Guidelines for the Invasive Vector of Thousand Cankers Disease of Walnut," Apr. 2012 University of California Agriculture and Natural Resources, Statewide Integrated Pest Management Program, pp. 1-11.
Seybold SJ, et al., "Thousand cankers disease. USDA Forest Service, Northeastern Area State and Private Forestry Pest Alert," 2011 NA-PR-02-10, May 2010, reprinted Aug. 2010 and Oct. 2011, 2 pp.
Seybold SJ, et al., "Diurnal flight response of the walnut twig beetle, *Pityophthorus juglandis*, to pheromone-baited traps in two northern California walnut habitats," 2012 Pan-Pacific Entomol 88(2):231-247.
Tisserat N, et al., "Black walnut mortality in Colorado caused by the walnut twig beetle and thousand cankers disease," 2009 Plant Health Progress.
Tisserat N, et al., "Thousand cankers disease is widespread on black walnut, *Juglans nigra*, in the western United States," 2011 Online. Plant Health Progr. (Published Jun. 30, 2011) doi:10.1094/PHP-2009-0811-01-RS.).
Zar J H, "Biostatistical Analysis," 5th Ed. 2010 Pearson Prentice Hall, Englewood Cliffs, New Jersey.
Nelson LJ, et al., "Identification of semiochemicals for detection and monitoring of the walnut twig beetle, *Pityophthorus juglandis* (Coleoptera:Scolytidae)," 58th Meeting of the Entomological Society of America, Dec. 15, 2010.
Francese, J.A., et al., "Efficacy of multifunnel traps for capturing emerald ash borer (Coleoptera: Buprestidae): Effect of color, glue, and other trap coatings," 2011 Journal of Economic Entomology 104, pp. 901-908.

* cited by examiner

*Primary Examiner* — Robert T Crow
*Assistant Examiner* — John P Nguyen
(74) *Attorney, Agent, or Firm* — John D. Fado; Lesley D. Shaw; Janet I. Stockhausen (57) ABSTRACT

Disclosed are methods which include exposing a beetle of the species *Pityophthorus juglandis* and/or treating surfaces susceptible to infestation by the species or to infection by *Geosmithia morbida* with compositions including one or more semiochemicals capable of being produced by *Pityophthorus juglandis*. The semiochemicals can be 3-methyl-2-buten-1-ol, conophthorin or chalcogran. Also disclosed are compositions and systems used in the methods.

9 Claims, 7 Drawing Sheets

Flight response of WTB to compounds "X" and "Z"

"X" + "Z"    b 0.08  0.08 b

"X"    a 2.1    4.3 a

"Z"    b    b unbaited control    b    b

Male response — Female response

No. of *P. juglandis*/day (mean ± S.E.)

METHODS OF MONITORING AND CONTROLLING THE WALNUT TWIG BEETLE, *PITYOPHTHORUS JUGLANDIS*

CROSS-REFERENCE TO RELATED APPLICATIONS

This application claims priority from U.S. provisional patent application Ser. No. 61/508,441, filed on Jul. 15, 2011, the entire disclosure of which is hereby incorporated by reference.

REFERENCE TO GOVERNMENT RIGHTS

This invention was made with government support under grant numbers 10-CA-11272172-055 and 10-JV-11272172-092 awarded by the United States Department of Agriculture. The government has certain rights in the invention.

BACKGROUND

The walnut twig beetle (WTB), *Pityophthorus juglandis* Blackman (Coleoptera: Scolytidae), is associated with thousand cankers disease of walnut (*Juglans* sp.). Spores of a newly identified fungus, *Geosmithia morbida*, are introduced into the phloem when the beetles bore through the bark. (See Kolařik, M., Freeland, E., Utley, C., and Tisserat, N. 2011. *Geosmithia morbida* sp. nov., a new phytopathogenic species living in symbiosis with the walnut twig beetle (*Pityophthorus juglandis*) on *Juglans* in USA. *Mycologia* 103: 325-332.) The infection results in numerous cankers that eventually kill the tree, often within 3 years of the first appearance of symptoms.

Thousand cankers disease is a walnut disease of national significance that threatens the health and longevity of a variety of walnut species and their rootstocks, including walnuts of the edible crop (*Juglans regia*) industry and walnuts of the timber (*Juglans nigra*) industry. (See Tisserat, N., Crenshaw, W., Leatherman, D., Utley, C., and Alexander, K. 2009. Black walnut mortality in Colorado caused by the walnut twig beetle and thousand cankers disease. *Plant Health Progress*. Published 11 August 2009; Seybold, S. J., Haugen, D., O'Brien, J., and Graves, A. D. 2011. Thousand cankers disease. USDA Forest Service, Northeastern Area State and Private Forestry Pest Alert, NA-PR-02-10, May, 2010, reprinted August 2010 and October 2011, 2 pp.; Tisserat N., Cranshaw W., Putnam, M., Pscheidt, J. Leslie, C. A., Murray, M., Hoffman, J., Barkely, Y., Alexander, K., and Seybold, S. J. 2011. Thousand cankers disease is widespread on black walnut, *Juglans nigra*, in the western United States. Online. *Plant Health Progr.* (Published Jun. 30, 2011) doi:10.1094/PHP-2009-0811-01-RS.). Notably, one of the most susceptible species, *Juglans nigra* is an economically valuable hardwood tree species in North America, with a standing timber value in the range of $500 billion. The WTB, vector of the fungus causing the disease, is expanding its range and causing increased tree mortality in the western U.S. and was recently discovered near Knoxville, Tenn. (July 2010), Richmond, Va. (July 2011), and Bucks Co., Pa. (August 2011). (See Seybold, S. J., Coleman, T. W., Dallara, P. L., Dart, N. L., Graves, A. D., Pederson, L., and Spichiger, S.-E. 2012a. Recent collecting reveals new state records and the extremes in the distribution of the walnut twig beetle, *Pityophthorus juglandis* Blackman (Coleoptera: Scolytidae), in the United States. *Pan-Pacific Entomol.* (accepted, in press May 30, 2012) and Seybold, S. J., Haugen, D., O'Brien, J., and Graves, A. D. 2011. Thousand cankers disease. USDA Forest Service, Northeastern Area State and Private Forestry Pest Alert, NA-PR-02-10, May 2010, reprinted August 2010 and October 2011, 2 pp.) Northern California black walnut, *Juglans hindsii*, is rapidly succumbing to this threat in California. Id. Unfortunately, little is known about the semiochemicals that may mediate the colonization of host trees by WTB. Moreover, WTB is an unusual species in that it is an angiosperm-infesting *Pityophthorus*, as compared to other twig beetles, which infest conifers, and in that it colonizes the largest branches and main stem of the tree, whereas other species are confined to the twigs. Few products or methods exist for detecting and combating thousand cankers disease of walnut and none have demonstrated any significant effectiveness at combating the disease.

SUMMARY

Provided herein are methods of monitoring and controlling *Pityophthorus juglandis*. Also disclosed are compositions and systems for use with the methods.

Certain aspects of the invention are based, at least in part, on the inventors' discovery that certain semiochemicals, including 3-methyl-2-buten-1-ol, conophthorin (7-methyl-1,6-dioxaspiro[4,5]decane), and chalcogran (2-ethyl-1,6,-dioxaspiro [4,4]nonane), are produced by the walnut twig beetle (WTB), *Pityophthorus juglandis*. Moreover, the inventors have discovered that 3-methyl-2-buten-1-ol can act as an attractant for *Pityophthorus juglandis* and chalcogran and (−)-trans-conophthorin can act as repellants for *Pityophthorus juglandis*. Notably, the compound, 3-methyl-2-buten-1-ol, has not previously been found to be associated with any members of the family Scolytidae (bark and ambrosia beetles) and neither chalcogran nor either enantiomer of conophthorin has previously been found to be associated with the species *Pityophthorus juglandis*.

The disclosed methods use compositions that include 3-methyl-2-buten-1-ol, conophthorin, and/or chalcogran, and possibly, other semiochemicals or components. Thus, various embodiments of the methods can be used for monitoring, detecting, trapping, controlling and/or reducing populations of *Pityophthorus juglandis*. The methods can be used for inhibiting or preventing the infestation of surfaces (including the surfaces of species of the genus *Juglans*) susceptible to infestation by *Pityophthorus juglandis*; inhibiting or preventing the infection of such surfaces by *Geosmithia morbida* by inhibiting beetle landing; or inhibiting or preventing the mortality of such surfaces by thousand cankers disease.

Exemplary benefits of at least some embodiments of the disclosed methods include selective detection of populations of *Pityophthorus juglandis*; less toxicity to applicators, environments and non-targeted organisms; greater specificity and effectiveness for behavioral manipulation of the targeted beetles; and lower costs of manufacture and application as compared to existing generic methods of insect control (e.g., insecticides, ethanol baits, insect-infested or diseased tree removal).

In one aspect, methods are provided that include exposing a beetle of the species *Pityophthorus juglandis* to a composition including certain semiochemicals and/or treating surfaces susceptible to infestation by the species with the composition. The semiochemicals include those that are capable of being produced by *Pityophthorus juglandis*, such as 3-methyl-2-buten-1-ol, conophthorin, and chalcogran. Other exemplary semiochemicals, combinations of semiochemicals, and other additives for the compositions are described herein. Thus, in another aspect, the compositions for use with the methods are also provided.

In another aspect, systems including the compositions are also provided. The systems may be configured for use in the treatment of surfaces susceptible to infestation by *Pityophthorus juglandis*. The systems may include or may be coupled to conventional components (e.g., release devices and traps) used for monitoring or controlling insects or treating surfaces susceptible to infestation by insects. The systems may be configured to provide certain release rates of the semiochemicals within the compositions.

Also described are exemplary surfaces susceptible to infestation by *Pityophthorus juglandis*.

Other principal features and advantages of the invention will become apparent to those skilled in the art upon review of the following drawings, the detailed description, and the appended claims.

DETAILED DESCRIPTION

Provided herein are methods of monitoring and controlling *Pityophthorus juglandis*. Also disclosed are compositions and systems for use with the methods.

The disclosed methods include exposing a *Pityophthorus juglandis* to a composition including certain semiochemicals (behaviorally active compounds) and/or treating surfaces susceptible to infestation by the species with the composition. The semiochemicals include those which are capable of being produced by *Pityophthorus juglandis* with or without feeding on the host, *Juglans*, phloem or bark. Some semiochemicals may be derived from the host *Juglans* phloem and bark itself. By "capable of being produced" it is meant that the semiochemicals are those that are produced naturally by *Pityophthorus juglandis*. However, the actual semiochemical used in the disclosed methods need not have been produced by *Pityophthorus juglandis* (although the semiochemical may be one that has been separated and purified from beetle extracts). Instead, the semiochemical may be produced naturally by other ecologically relevant organisms (e.g., *Geosmithia morbida*), may be synthesized in a laboratory by humans and may be commercially available. Exemplary semiochemicals include 3-methyl-2-buten-1-ol, 3-methyl-3-buten-1-ol, 3-methyl-1-butanol, 3-methyl-2-butenal, (−)-trans-conophthorin, (+)-trans-conophthorin, or chalcogran. Combinations of these semiochemicals in the compositions are possible.

In some embodiments, the semiochemical is 3-methyl-2-buten-1-ol. In other embodiments, 3-methyl-2-buten-1-ol is combined with one or more semiochemicals selected from 3-methyl-3-buten-1-ol, 3-methyl-1-butanol or 3-methyl-2-butenal. In other embodiments, the semiochemical is selected from a racemic mixture of conophthorin, (−)-trans-conophthorin, a racemic mixture of chalcogran, or combinations thereof.

Compositions may also include other components such as other semiochemicals that may or may not be produced by *Pityophthorus juglandis*. Two such semiochemicals are verbenone and trans-verbenol. Other possible components are provided in the Examples below.

The compositions may consist of any of the semiochemicals or components disclosed above or combinations thereof. The compositions may consist essentially of any of the semiochemicals or components disclosed above or combinations thereof. The latter compositions may also include antioxidants (e.g., about 0.5% weight/weight) to inhibit oxidation of the semiochemical(s) and/or preservatives to inhibit bacterial or fungal growth in the compositions and such compositions may still be considered to "consist essentially of" the semiochemical(s) and, if present, other components. In some embodiments, the composition consists of, or consists essentially of, 3-methyl-2-buten-1-ol. In some embodiments, the composition consists of, or consists essentially of, 3-methyl-2-buten-1-ol and one or more semiochemicals selected from 3-methyl-3-buten-1-ol, 3-methyl-1-butanol or 3-methyl-2-butenal. In some embodiments, the composition consists of, or consists essentially of, racemic conophthorin. In some embodiments, the composition consists of, or consists essentially of, (−)-trans-conophthorin. In some embodiments, the composition consists of, or consists essentially of, racemic chalcogran. In some embodiments, the composition consists of, or consists essentially of, (−)-trans-conophthorin and one or more semiochemicals selected from (+)-trans-conophthorin or racemic chalcogran.

The compositions may be formulated in a variety of ways. Formulations used for delivering conventional insecticides or conventional semiochemicals may be used. Exemplary formulations include aerosols, slurries, plastic flakes and microencapsulated beads. Thus, the compositions may include other materials (e.g., polymers, solvents, gases, etc.) for achieving such formulations. The compositions may include such other materials and may still be considered to "consist essentially of" the semiochemical(s) therein and, if present, other components.

The compositions may be provided as part of a system, which may be configured for use in the treatment of surfaces susceptible to infestation by *Pityophthorus juglandis*. The systems may vary and may include conventional components used for monitoring or controlling insects or treating surfaces susceptible to infestation by insects.

By way of example only, a system may include the composition and a release device configured to hold the composition and to release the composition and/or semiochemical(s) therein at a specified release rate over a period of time (e.g., hours, days, weeks, months). The form of the release device is not particularly limited and can include containers such as a bag, a pouch, a bottle, a microcentrifuge tube, or a bubble cap. These containers and others may be made of a polymer such as low density polyethylene (LDPE), polyethylene, polyvinylchloride and the like. At least some of these containers, e.g., a bubble cap, may further include a substrate, e.g., a sponge, on which the composition is applied. Release devices having a substantially flat form, such as a strip, a card, or a panel are also possible. In such release devices, the strip, card, panel, etc. provides a support substrate for holding the composition. Release devices can be permeable such that they include an opening(s) or are made of a material that allows the composition and/or semiochemical(s) therein to be released from, or through, at least a portion of the release device into the atmosphere. A plurality of release devices may be used, configured in a grid pattern among surfaces susceptible to infestation by *Pityophthorus juglandis* (e.g., a population of trees of the genus *Juglans*).

As another example, a system may include the composition (with or without the release device) and a trap configured to capture insects, including *Pityophthorus juglandis*. Exemplary traps are known and include sticky card traps having a variety of colors (e.g., clear, gray, black, yellow) or funnel traps (e.g., a Lindgren funnel trap) or intercept panel traps. (See Andrew D. Graves, Edward H. Holsten, Mark E. Ascerno, Kenneth P. Zogas, John S. Hard, Dezene P. W. Huber, Robert A. Blanchette, Steven J. Seybold 2008. Protection of spruce from colonization by the bark beetle, Ips perturbatus, in Alaska. Forest Ecology and Management 256: 1825-1839.) In such systems, the composition (with or without the release device) is coupled to (e.g., attached to, integrated into, or placed in the vicinity of) the trap.

As another example, a system may include the composition, a container configured to hold the composition, and a device configured to spray or otherwise apply the composition directly onto surfaces susceptible to infestation by *Pityophthorus juglandis* or to spray or otherwise infuse the composition into the atmosphere surrounding such surfaces.

Exemplary specific systems include a polyethylene bottle or a LDPE pouch containing 3-methyl-2-buten-1-ol suspended over, or attached to, a clear sticky card trap. Another exemplary specific system includes a polyethylene bottle or a LDPE pouch containing 3-methyl-2-buten-1-ol attached to a 4-unit Lindgren funnel trap. Another exemplary specific system includes a polyethylene microcentrifuge tube, a LDPE pouch, or a polyvinylchloride bubble cap containing one or more repellant semiochemicals, e.g., racemic conophthorin, (−)-trans-conophthorin or racemic chalcogran. Other specific systems are described in the Examples below.

The systems (and/or the release devices and traps) may be further configured to provide certain release rates of the compositions within the systems or the semiochemicals, and, if present, other components, within the compositions. In some embodiments, the release rate is in the range from about 0.2 µg/day to about 200 g/day. This includes embodiments in which the release rate is in the range from about 0.2 µg/day to about 200 mg/day; about 1 µg/day to about 150 mg/day; about 10 µg/day to about 100 mg/day; about 100 µg/day to about 50 mg/day; about 1 mg/day to about 50 mg/day; about 2 mg/day to about 30 mg/day; or about 5 mg/day to about 20 mg/day. This further includes embodiments in which the release rate is in the range from about 0.2 mg/day to about 200 mg/day; about 0.5 mg/day to about 80 mg/day; about 0.5 mg/day to about 10 mg/day; about 0.5 mg/day to about 7 mg/day; about 0.5 mg/day to about 5 mg/day; about 0.5 mg/day to about 4 mg/day; or about 0.5 mg/day to about 2 mg/day. The release rate of the individual semiochemicals and the release rate of the other components, if present, may be the same or different. The release rate of different semiochemicals within the compositions may be the same or different.

Depending upon the nature of the system, the step of treating a surface susceptible to infestation by *Pityophthorus juglandis* may include positioning the system on or in the vicinity of the surface or applying the system to the surface. Similarly, the step of treating a surface susceptible to infestation by *Pityophthorus juglandis* may include positioning the composition on or in the vicinity of the surface or applying the composition to the surface. By "vicinity" it is meant that the system or composition is sufficiently near the surface to achieve any of the results disclosed herein (e.g., detecting, trapping, controlling and/or reducing populations of *Pityophthorus juglandis* and/or inhibiting or preventing infestation of surfaces susceptible to infestation by *Pityophthorus juglandis*, infection of such surfaces by *Geosmithia morbida* or the mortality of such surfaces by thousand cankers disease).

Specific treating steps include positioning a system including a polyethylene bottle, a LDPE pouch, or a LDPE bubble cap containing 3-methyl-2-buten-1-ol attached to a 4-unit Lindgren funnel trap in the vicinity of one or more trees of the genus *Juglans* at a certain height above the ground. Another specific treating step includes positioning a system including a polyethylene bottle, a LDPE pouch, or a LDPE bubble cap containing 3-methyl-2-buten-1-ol suspended over, or attached to, a clear sticky card trap in the crown of a tree of the genus *Juglans* at a certain height above the ground. Another specific treating step includes spraying a composition including one or more repellant semiochemicals, e.g., racemic conophthorin, (−)-trans-conophthorin or racemic chalcogran, directly onto one or more trees of the genus *Juglans* or into the atmosphere surrounding such trees. Other specific treating steps are described in the Examples below.

Some embodiments of the methods can involve treating at least one surface (e.g., one tree) as disclosed herein to achieve any of the results disclosed herein in at least one other, different surface (e.g., a nearby population of trees). At least some such embodiments may provide a "trap tree" tactic in which aggregation of WTB is elicited in one or more trees in order to inhibit infestation of a nearby population of trees. By way of example only, one tree of the genus *Juglans* (which may or may not be a dying tree) may be treated by positioning a trap or a release device containing 3-methyl-2-buten-1-ol on the stem or in the crown of the tree, or by applying 3-methyl-2-buten-1-ol directly to the tree. Such a treatment provides a "trap tree" such that the treated tree traps beetles of the species *Pityophthorus juglandis*. The infested trap tree may be removed before *Pityophthorus juglandis* emerges and/or may be treated with an insecticide to kill the beetles. By diverting the beetles from other nearby trees and lowering the population of the pest, the trap tree may inhibit infestation of these nearby trees.

Other embodiments of the methods may provide a "push-pull" tactic, in which compositions including one or more repellant semiochemicals are positioned within a group of trees ("push") and traps baited with an attractant semiochemical are positioned around the group of trees ("pull").

The types of semiochemicals used in the compositions, the presence of other components in the compositions, the relative amounts of the semiochemicals and other components, the release rates of the semiochemicals and other components, the nature of the system (e.g., type of release device or trap), and the position or application of the system (or composition) on a surface to be treated each may be adjusted in order to achieve certain results. For example, these variables may be adjusted in order to increase the number of beetles attracted to the composition, system or surface. Similarly, these variables may be adjusted in order to decrease the number of beetles present at the composition, system or surface or to provide a certain flight response (e.g., number of beetles per day). The variables may also be adjusted in order to inhibit or prevent infestation of surfaces susceptible to infestation by *Pityophthorus juglandis*, inhibit or prevent infection of such surfaces by *Geosmithia morbida* or inhibit or prevent mortality of such surfaces by thousand cankers disease as compared to untreated surfaces. Standard methods may be used to measure beetle counts and flight response, to evaluate infestation, and to measure the rate of infection and rate of mortality.

The disclosed methods may use effective amounts of the disclosed compositions. By "effective amount" it is meant that amount which achieves any of the results disclosed herein.

The disclosed methods may include other steps such as baiting a trap with any of the disclosed compositions, trapping a beetle of the species *Pityophthorus juglandis* and/or counting trapped beetles.

Surfaces susceptible to infestation by *Pityophthorus juglandis* can include trees and components of trees, including, but not limited to bark, logs, boards with or without bark, branches and twigs. Exemplary trees include species of the genus *Juglans*. Exemplary species include *Juglans regia*, *Juglans nigra*, *Juglans hindsii*, *Juglans cinerea* and *Juglans californica*. Trees may be those in residential or urban settings, in orchards, plantations, forests and the like.

As noted above, at least certain embodiments of the methods provide a way of detecting and/or trapping populations of *Pityophthorus juglandis*. Such methods themselves may facilitate the inhibition or prevention of infestation of surfaces susceptible to infestation by *Pityophthorus juglandis*, the inhibition or prevention of infection of such surfaces by *Geosmithia morbida* or the inhibition or prevention of mortality of such surfaces by thousand cankers disease by identifying those populations of surfaces which are under threat and which may require further treatment with the disclosed methods or with other treatment methods.

Also provided are methods of making any of the systems disclosed herein. One such method includes introducing any of the disclosed compositions onto, or into, any of the disclosed release devices. Another such method includes coupling any of the disclosed compositions or release devices containing the compositions (e.g., attaching to, integrating into, or placing in the vicinity of) to any of the disclosed traps.

The methods, compositions, and systems will be understood more readily by reference to the following examples, which are provided by way of illustration and are not intended to be limiting.

EXAMPLES

The following abbreviations are used throughout the Examples.
WTB=walnut twig beetle
*P. juglandis*=*Pityophthorus juglandis*
*J. hindsii*=*Juglans hindsii*
*J. regia*=*Juglans regia*
*J. nigra*=*Juglans nigra*
X=3-methyl-2-buten-1-ol
X-1=3-methyl-2-butenal
X-2=3-methyl-1-butanol
X-3=3-methyl-3-buten-1-ol
−Y=(−)-trans-conophthorin
+Y=(+)-trans-conophthorin
Y=racemic conophthorin
Z=racemic chalcogran
GC-MS=Gas Chromatography-Mass Spectrometry
GC-EAD=Gas Chromatography-Electroantennal Detection
d=day
LDPE=low density polyethylene
TCD=Thousand Cankers Disease Example 1

Collection of Semiochemicals from WTB; Identification of Semiochemicals; Field Bioassays of Semiochemicals Methods and Materials
Collection of Insects.
Uninfested *Juglans hindsii* and immature and adult *P. juglandis* were collected on separate occasions for producing volatile extracts (Table 1). The insects were collected in cut, infested logs and the logs were placed into emergence cages. (See Browne, L. E. 1972. An emergence cage and refrigerated collector for wood-boring insects and their associates. *J. Econ. Entomol.* 65: 1499-1501.) Emerging adult *P. juglandis* were separated from other subcortical insects under a dissecting microscope and the sexes were separated based on the pubescence on the female frons and minute spines/tubercles on the male elytral declivity. (See Seybold, S. J., Dallara, P. L., Hishinuma, S. M., and Flint, M. L. Detecting and Identifying the Walnut Twig Beetle: Monitoring Guidelines for the Invasive Vector of Thousand Cankers Disease of Walnut, University of California Agriculture and Natural Resources, Statewide Integrated Pest Management Program, 11 pp., Apr. 30, 2012). Adults were stored at 4° C. on dry paper toweling in plastic or glass containers or in Ziploc bags prior to use in the volatile collection step (see below). Green (uninfested) branches were removed from live *J. hindsii* trees and cut into smaller lengths several days prior to initiating the aerations (Table 1).

TABLE 1

Collection of *Pityophthorus juglandis* in California for production of volatiles for semiochemical analyses[a]

| Host | County | Locality | Coordinates, elevation | Comments |
| --- | --- | --- | --- | --- |
| *Juglans hindsii* | Sutter | Rio Oso, 0.25 km E/NE intersection of Hwy 70 and Rio Oso Road, John Taresch Farm | 38°57'49.834"N, 121°32'17.740"W, 49.4 m | Cut logs from large branches from a firewood pile |
| *J. hindsii* × *regia* | Yolo | UC-Davis Walnut Collection, Tree #R8T3, Hutchison Drive | 38°32.357' N, 121°47.774' W, 21.6 m | Paradox (*J. hindsii* × *regia*) rootstock section from a tree that died VII-2009 |

[a]Green (uninfested) branches of *Juglans hindsii* (2-4 cm diameter) were removed from live trees and cut into shorter sections (20-25 cm long) (Yolo Co., Davis, West Russell Blvd., 38°32'49.1958" N, 121°47'44.4006" W).

Volatile Collection.

Volatiles from male and/or female WTB feeding on *J. hindsii* branches, and from the branches alone, were collected on SUPER Q (80/100 mesh, Part #2735, Alltech Associates Inc., Deerfield, Ill., USA) and PORAPAK Q (50/80 mesh size, Supelco, Bellefonte, Pa.) columns. The first set of aerations was conducted over an 8 day period. Five small green branches were placed into dry fish bowls with 100 males, 100 females, and 100 males and 100 females, or no beetles, and the beetles were allowed to feed for a feeding period of between one and four days. New beetles were added if dead ones were found in the bowls.

After the feeding period, the branches were transferred to 500 ml glass storage bottles fitted with a ground-glass side arm. The flow rate of compressed air through these bottles was 30 ml/min and the air passed through 1 g PORAPAK Q filtration columns. On the side arm, a small collection column of SUPER Q (~115 mg in a short glass column, plugged on each end with glass wool) was used to trap the effluent. (See Bartelt, R. J., Kyhl, J. F., Ambourn, A. K., Juzwik, J., and Seybold, S. J. 2004. Male-produced aggregation pheromone of *Carpophilus sayi*, a nitidulid vector of oak wilt disease, and pheromonal comparison with *Carpophilus lugubris*. *Agricultural and Forest Entomology* 6:39-46.) These columns were extracted with enough pentane to yield 100 μl samples. They were extracted secondarily with methylene chloride to also yield 100 μl samples, which contained a mixture of both solvents. All solvent was driven off the columns during the second extraction step by using a pipette bulb.

The following pentane extracts were obtained: (1) SUPER Q aeration of walnut (*Juglans hindsii*) alone for 14.5 hr; (2) SUPER Q aeration of walnut (*Juglans hindsii*) with male *P. juglandis* for 14.5 hr; (3) SUPER Q aeration of walnut (*Juglans hindsii*) with female *P. juglandis* for 14.5 hr; (4) SUPER Q aeration of walnut (*Juglans hindsii*) with male *P. juglandis* for 23 hr; (5) SUPER Q aeration of walnut (*Juglans hindsii*) with female *P. juglandis* for 23 hr; (6) SUPER Q aeration of walnut (*Juglans hindsii*) with male and female *P. juglandis* for 23 hr; and (7) SUPER Q aeration of walnut (*Juglans hindsii*) with male and female *P. juglandis* for 45 hr.

Twenty-seven live males and 25 live females were retained for GC-EAD of these extracts.

In order to collect more material for analysis, larger scale aerations were conducted next. Branches of *J. hindsii* were cut into 20-25 cm lengths and placed into 19 l glass carboys. Male and female beetles (>1,000 of each sex) were introduced into separate carboys and allowed to begin feeding for a feeding period of 4 days. Another carboy contained uninfested branches. Air was filtered through activated charcoal and passed through the carboys at 4 l/min. The volatiles were collected on 15 g of PORAPAK Q for 5 to 8 days. At the end of collection period the PORAPAK Q columns were replaced with clean ones and the process was continued for another week. Two columns containing the retained volatiles were sealed with Teflon tape and placed in a freezer at −35° C. Columns were extracted by passing 350 ml pentane through the adsorbant and concentrating the eluant to approximately 9 ml by using a Kuderna-Danish apparatus. The Porapak was extracted a second time with methylene chloride, and processed identically.

Semiochemical Identification.

GC-MS analyses were performed on an Agilent 6890 GC coupled with the 5973 MSD, with Agilent Chemstation data analysis software G1701CA version C.00.00 (Agilent, Santa Clara, Calif.). The GC-MS was equipped with a DB-WAX fused silica capillary column (60 m×0.25 mm ID, 0.25 μm film thickness) and operated in splitless mode. Each extract was analyzed by using a temperature program from 37° C. to 195° C. at 2° C./min with a final hold of 5 min. Helium was the carrier gas and the flow rate was 1 ml/min. Electron impact (EI) mass spectra were obtained at 70 eV. Compounds were identified by comparison with library spectra and authentic standards. The commercial sources of the authentic standards were: 3-methyl-2-buten-1-ol, ≥98% (W364703, SAFC, St. Louis Mo.); 3-methyl-2-butenal, 97% (W364607, Aldrich, St. Louis Mo.); 3-methyl-1-butanol, 98.5% (320021, Sigma-Aldrich, St. Louis Mo.), 3-methyl-3-buten-1-ol, 97+% (W519308, SAFC, St. Louis Mo.), racemic conophthorin [(5S,7S)-7-methyl-1,6-dioxaspiro[4,5]decane] (300000492, Contech Enterprises Inc., Delta, British Columbia, Canada), racemic chalcogran (2-ethyl-1,6,-dioxaspiro[4,4]nonane) >96.0% (78127, Sigma, St. Louis Mo.).

Gas Chromatography-Electroantennal Detection (GC-EAD).

GC-EAD analysis was performed on the extract of walnut (*Juglans hindsii*) with male and female *P. juglandis* feeding for 45 hr (pentane extract (7)). The sample was analyzed with an HP5890 GC with the following conditions: DB-5 column 30 m×0.32, oven 50° C. for 1 min, temperature programmed at 20° C./min to a final temperature of 280° C.

Field Bioassays of Semiochemicals.

To test the attractiveness of the various compounds of interest, some of the commercially available materials listed above were poured into 15 ml capped polyethylene bottles (Product #s A1-1050/002, A1-1055/002; Contech Enterprises Inc., Delta, British Columbia, Canada) and attached to yellow sticky card traps (Trécé, Adair, Okla.). In addition, synthesized (+) and (−) enantiomers of trans-conophthorin were tested in 400 μl polyethylene Eppendorf microcentrifuge tubes. Four field studies were conducted (Table 2) that tested the flight responses to: 3-methyl-2-buten-1-ol and related isomers (Field Test 1); 3-methyl-2-buten-1-ol with and without racemic trans-conophthorin (Field Test 2); 3-methyl-2-buten-1-ol with and without the purified enantiomers of trans-conophthorin (Field Test 3); and 3-methyl-2-buten-1-ol with and without racemic chalcogran (Field Test 4).

TABLE 2

Field tests of compounds identified in volatiles from male and female WTB feeding on *J. hindsii*[a,b]

Field Test 1, Davis, Yolo Co., CA

X
X-1
X-2
X-3
U

Field Test 2, Davis, Yolo Co., CA

X
X-Y
Y

Field Test 3, Pleasanton, Alameda Co., CA

X
X + (−)-Y
X + (+)-Y
(−)-Y
(+)-Y
U

Field Test 4, Davis, Yolo Co., CA

X
Z
X + Z
U

[a] X = 3-methyl-2-buten-1-ol; X-1 = 3-methyl-2-butenal; X-2 = 3-methyl-1-butanol; X-3 = 3-methyl-3-buten-1-ol; U = unbaited; Y = racemic conophthorin; (−)-Y = (−)-trans-conophthorin; (+)-Y = (+)-trans-conophthorin; Z = racemic chalcogran
[b] In each test, one yellow sticky trap was baited with 15 ml of each compound listed, except for Y and Z which were released as ~100 μl amounts.

Seasonal Flight Patterns.

Trap catch data from yellow sticky traps baited with 15 ml polyethylene plastic bottles filled with 3-methyl-2-buten-1-ol were used to determine seasonal flight activity of WTB over a two-year period. Data are presented as the number of WTB per trap per day.

Statistical Analysis.

Field Tests 1-4 were each analyzed for treatment effect by using Friedman's non-parametric analysis of variance. (See Zar, J. H. 2010. Biostatistical Analysis, 5$^{th}$ Ed. Pearson Prentice Hall, New Jersey). Males and females were subjected to separate analyses. All treatments within experiments yielding a significant treatment effect were compared by using an a posteriori Nemenyi test (Zar 2010) with experimentwise $\alpha=0.05$. Sex ratios of responding WTB were determined using Cochran's method for unbiased sampling (See Cochran, W. G. 1977. Sampling Techniques, 3$^{rd}$ ed. John Wiley, New York), with 95% confidence intervals calculated by using the Clopper-Pearson method. (See Zar, J. H. 2010. Biostatistical Analysis, 5$^{th}$ Ed. Pearson Prentice Hall, New Jersey).

Results and Discussion

Semiochemical Identification.

GC-MS total ion chromatograms for various pentane extracts of male WTB, female WTB, and *J. hindsii* branches alone were obtained. Four compounds (in order of elution), 3-methyl-2-butenal (X-1), 3-methyl-1-butanol (X-2), 3-methyl-3-buten-1-ol (X-3) and 3-methyl-2-buten-1-ol (X), were identified in the pentane extracts from males feeding on *J. hindsii*. These compounds were not present in extracts from females or from uninfested branches. 3-methyl-2-buten-1-ol (X) was the most abundant of the four. Two other compounds of interest, conophthorin (Y) and chalcogran (Z), were found in extracts from both males and females, and small amounts of conophthorin were detected in the walnut alone.

GC-EAD.

Using GC-EAD, compounds X and Y were determined to be antennally active.

Field Bioassays of Semiochemicals.

Figure 1:
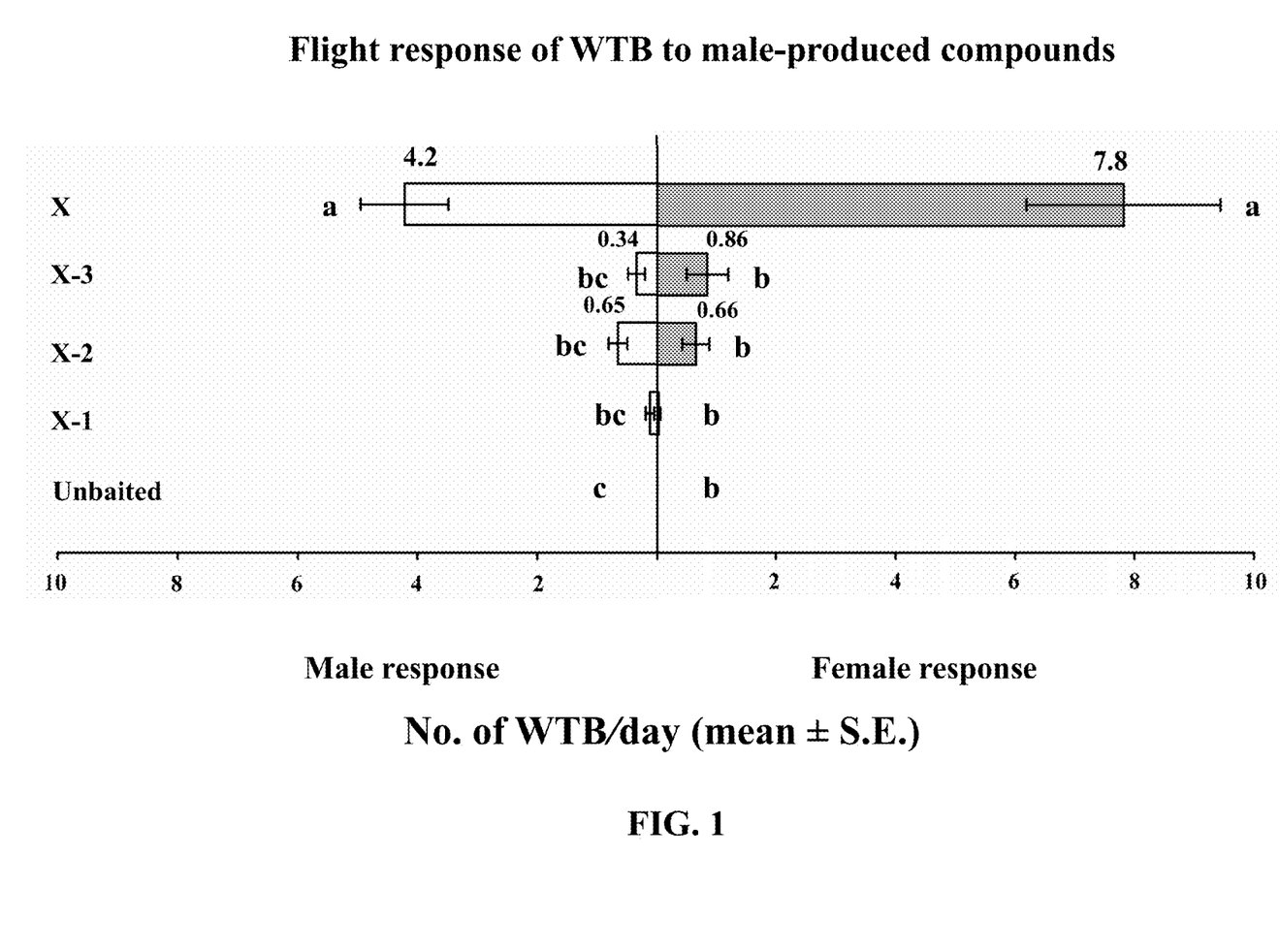
FIG. 1 shows the flight response of WTB to compounds X (3-methyl-2-buten-1-ol), X-1 (3-methyl-2-butenal), X-2 (3-methyl-1-butanol), and X-3 (3-methyl-3-buten-1-ol).

Using yellow sticky card traps, the compounds listed in Table 2 were evaluated alone and in combination, as flight attractants for the WTB. The results are shown in FIGS. 1-4. Of the male-produced compounds, 3-methyl-2-buten-1-ol, (X) was found to be attractive to males and females. Flight response of WTB to X, X-1, X-2, and X-3 was recorded over about a three month period in the summer in Davis, Yolo Co., Calif. Total trap catch in this experiment was 752 (271 male/481 female); catches to compound X were 233/438; catches to compound X-1 were 11/20; catches to compound X-2 were 23/21; catches to compound X-3 were 4/2; and catches to the unbaited control trap were 0/1, N=21. Friedman's non-parametric analyses of variance showed significant treatment effects for males (P<0.05) and females (P<0.01). Nemenyi's multiple comparisons (experimentwise $\alpha=0.05$ within each sex) are shown in FIG. 1. Proportions of females responding to X, X-1, X-2, and X-3 were 0.65, 0.65, 0.48, and 0.33, respectively, with overlapping 95% confidence intervals (0.615-0.689; 0.454-0.808; 0.325-0.633; and 0.043-0.778, respectively).

Figure 2:
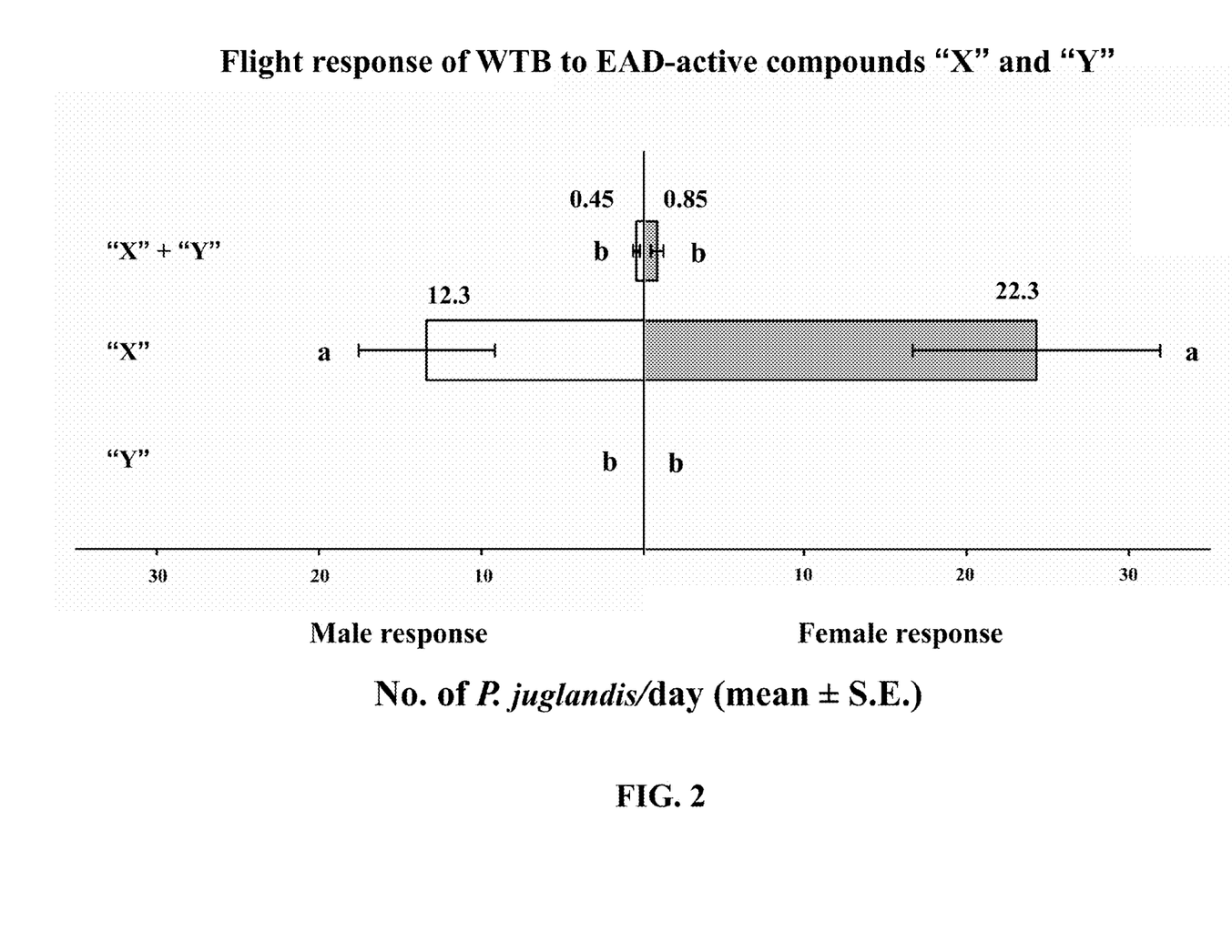
FIG. 2 shows the flight response of WTB to various combinations of compounds X (3-methyl-2-buten-1-ol) and Y (conophthorin).

Conophthorin (Y), which was found to be associated with both sexes and with the walnut alone, was found to be interruptive or repellent when tested as a racemic mixture. Flight response of WTB to various combinations of compounds X and Y was recorded over about a one month period in the late spring in Davis, Yolo Co., Calif. Total trap catch in this experiment was 733 (258 male/475 female); catches to compound X were 250/459 and catches to compounds X+Y were 8/16, N=16. Friedman's non-parametric analyses of variance showed significant treatment effects for males (P<0.001) and females (P<0.001). Nemenyi's multiple comparisons (experimentwise $\alpha=0.05$ within each sex) are shown in FIG. 2. Proportions of females responding to X and X+Y were 0.65 and 0.67, respectively, with overlapping 95% confidence intervals (0.611-0.683 and 0.447-0.844, respectively).

Figure 3:
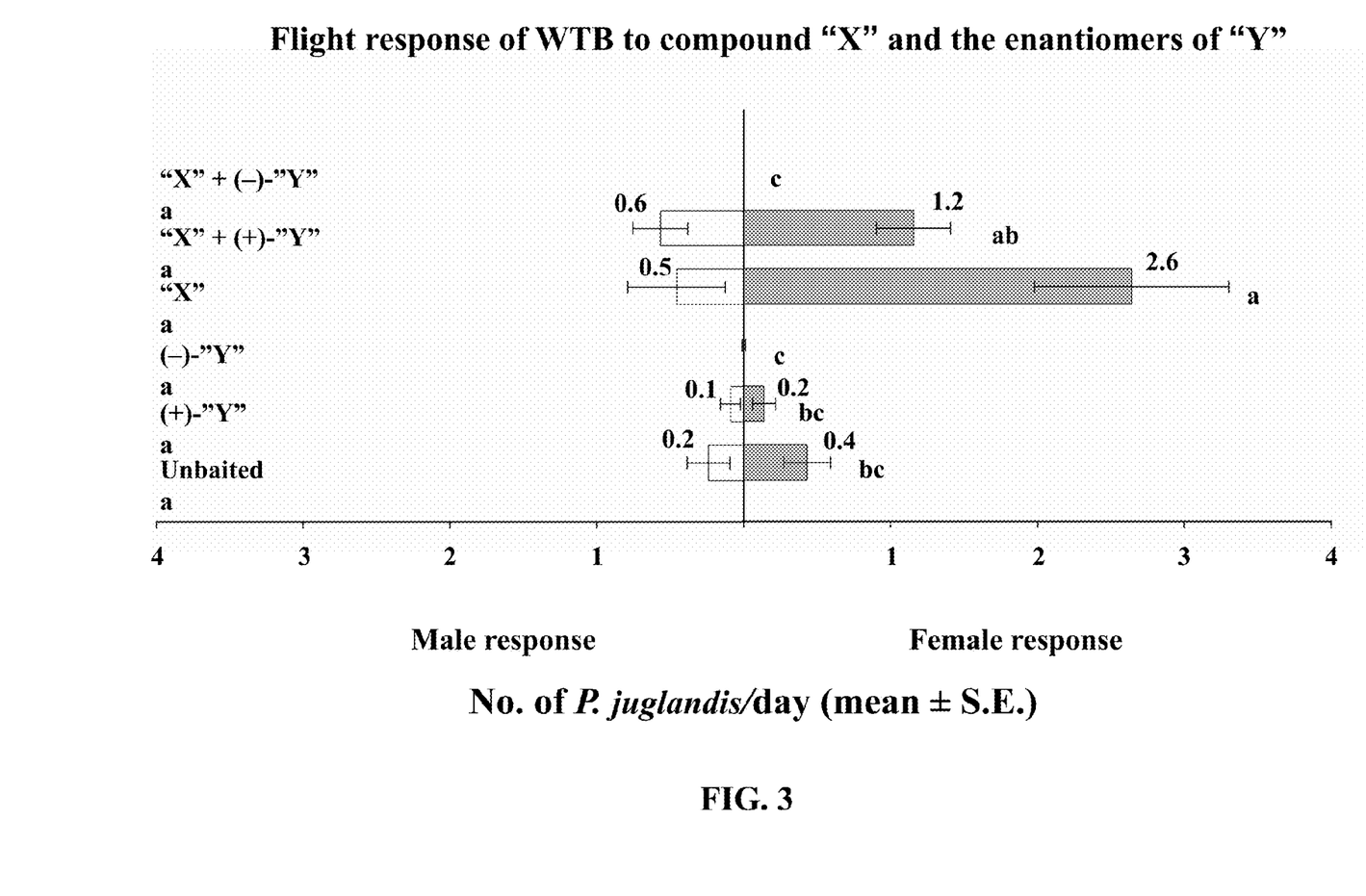
FIG. 3 shows the flight response of WTB to various combinations of compounds X (3-methyl-2-buten-1-ol) and the enantiomers of Y (conophthorin).

When the enantiomers of Y were tested separately, (−)-Y appeared to be the behaviorally active component. Flight response of WTB to various combinations of compounds X and the enantiomers of Y was recorded over about a one month period in the fall in Pleasanton, Alameda Co., Calif. Total trap catch in this experiment was 120 (32 male/88 female); catches to compound X were 12/47, and catches to compounds X+(+)-Y were 12/29, N=15. Friedman's non-parametric analyses of variance showed significant treatment effects for males (P<0.001) and females (P<0.001). Nemenyi's multiple comparisons (experimentwise $\alpha=0.05$ within each sex) are shown in FIG. 3. Proportions of females responding to X and X+Y were 0.80 and 0.71, respectively, with overlapping 95% confidence intervals (0.693-0.899 and 0.568-0.847, respectively).

Figure 4:
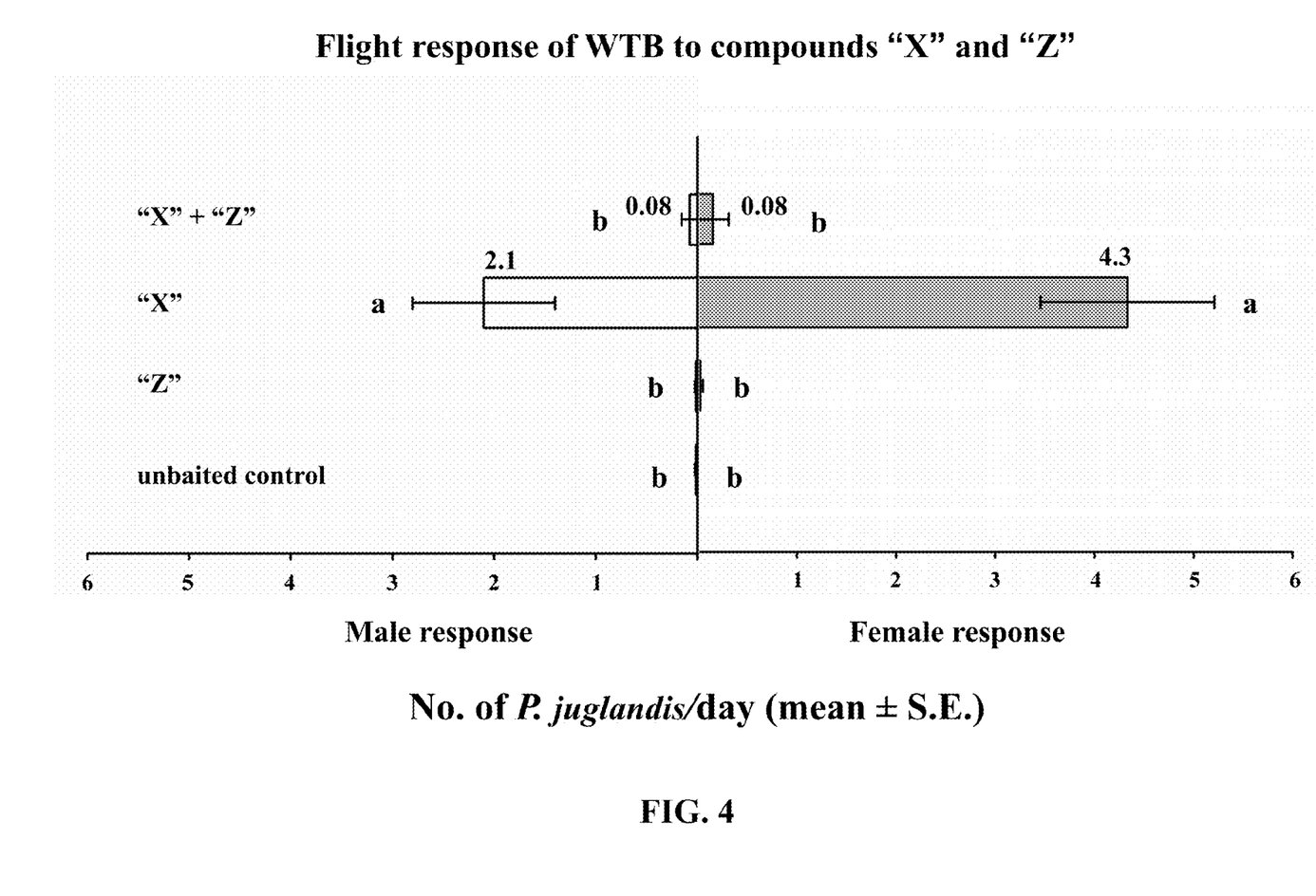
FIG. 4 shows the flight response of WTB to various combinations of compounds X (3-methyl-2-buten-1-ol) and Z (chalcogran).

Chalcogran (Z) was produced by both male and female WTB, but was not observed in uninfested branches. Chalcogran was found to be interruptive or repellent when tested as a racemic mixture. Flight response of WTB to various combinations of compounds X and Z was recorded over about a one month period in late summer in Davis, Yolo Co., Calif. Total trap catch in this experiment was 144 (46 male/98 female); catches to compound X were 43/94, catches to compound Z were ½, catches to compounds X+Z were ½, and catches to the unbaited control trap were ⅙, N=13. Friedman's non-parametric analyses of variance showed significant treatment effects for males (P<0.01) and females (P<0.001). Nemenyi's multiple comparisons (experimentwise $\alpha=0.05$ within each sex) are shown in FIG. 4. Proportions of females responding to X, Z, and X+Z were 0.69, 0.67, and 0.67, respectively, with overlapping 95% confidence intervals (0.601-0.763; 0.094-0.992; and 0.094-0.992, respectively).

Seasonal Flight Patterns.

The seasonal flight response of WTB to Compound X showed that peak flight was observed to occur in late May/early June. Female beetles were trapped as late as mid-November, and males and females were caught as early as January Example 2

Field Testing of Various Release Rates of 3-methyl-2-buten-1-ol and Field Bioassays of 3-methyl-2-buten-1-ol in Combination with Other Compounds Methods and Materials Field Testing of Various Release Rates of 3-methyl-2-buten-1-ol.

The flight response of WTB to two release rates of 3-methyl-2-buten-1-ol was tested at the Wolfskill Experimental Orchards (the *Juglans* collection of the USDA ARS National Clonal Germplasm Repository in Winters, Solano Co., Calif.) in late spring. The two release rates were: 1) 15-80 mg/d (depending on temperature, as per manufacturer's data), delivered from a commercially available LDPE plastic pouch (Product #300000736, RD-1039, Contech Enterprises Inc., Delta, BC, Canada); and 2) 5 mg/d (based on laboratory assessments at 25° C. and 30° C.), delivered from a 15 ml polyethylene bottle charged with 15 ml of 3-methyl-2-buten- 1-ol [≥98% chemical purity, product #W364703, SAFC (=Sigma-Aldrich), St. Louis Mo.]. The pouch or bottle was suspended in the middle of a 4-unit Lindgren funnel trap (Contech), attached to the funnel strut so it rested on the inside surface of the third funnel (counted from the trap top), without blocking the central axis/interior hole of the trap. The trap cup was filled with propylene glycol-based recreational vehicle/marine antifreeze to a depth of about 2.5 to 5 cm, and the traps were hung from poles at a height of approximately 3 m. (See Seybold, S. J., Dallara, P. L., Hishinuma, S. M., and Flint, M. L. Detecting and Identifying the Walnut Twig Beetle: Monitoring Guidelines for the Invasive Vector of Thousand Cankers Disease of Walnut, University of California Agriculture and Natural Resources, Statewide Integrated Pest Management Program, 11 pp., Apr. 30, 2012). The two treatments were replicated in four spatial blocks and the treatments were re-randomized between the two trap stations in a block each time the traps were emptied (nearly every day).

In a separate experiment, the flight response of WTB to six release rates of 3-methyl-2-buten-1-ol was tested at the same location in early summer. The six release rates were: 1) 165 mg/d, from a capped 15 ml polyethylene bottle with a 0.48 cm hole drilled in the side of the cap, charged with 15 ml 3-methyl-2-buten-1-ol (Sigma-Aldrich); 2) 15-80 mg/d from the commercial LDPE plastic pouch (Contech); 3) 5 mg/d from a capped 15 ml polyethylene bottle charged with 15 ml 3-methyl-2-buten-1-ol (Sigma-Aldrich); 4) 5 mg/d from a capped 15 ml polyethylene bottle charged with 1 ml 3-methyl-2-buten-1-ol (Sigma-Aldrich); 5) 0.2 mg/d from a 400 µl closed Eppendorf polyethylene microcentrifuge tube charged with 300 µl 3-methyl-2-buten-1-ol (Sigma-Aldrich); and 6) an unbaited control. The 15 ml polyethylene bottles were purchased from Contech Enterprises (product #100000582/583); the 400 µl polyethylene Eppendorf microcentrifuge tubes were purchased from Evergreen Scientific (product #214-3417-020, Los Angeles, Calif.). These release devices were attached to 4-unit Lindgren funnel traps as described above. The six treatments were replicated in three spatial blocks and the treatments were re-randomized among the six trap stations in a block each time the traps were emptied (nearly every day).

Field Bioassays of 3-methyl-2-buten-1-ol in Combination with Other Compounds.

The flight response of WTB to 3-methyl-2-buten-1-ol in combination with other compounds was also tested. The first experiment, conducted in mid-summer at Wolfskill Experimental Orchards, compared response to combinations of 3-methyl-2-buten-1-ol (release rate 15-80 mg/d plastic pouch, Contech) and two other compounds that were identified in the volatiles produced by male WTB feeding on *J. hindsii*: 3-methyl-3-buten-1-ol (X-3) and 3-methyl-1-butanol (X-2) (Table 3, Field Test 1). 3-Methyl-2-buten-1-ol (≥98% chemical purity, product # W364703); 3-methyl-3-buten-1-ol (97% chemical purity, product #W519308-1 KG); and 3-methyl-1-butanol (98.5% chemical purity, product #320021-1L) were all purchased from Sigma-Aldrich (SAFC), St. Louis, Mo. Compounds X-3 and X-2 (300 µl of each) were loaded in 400 µl Eppendorf microcentrifuge tubes (Evergreen) and their estimated release rates were 1.76 mg/d at 25° C. This release rate was selected to match the component ratios of 3-methyl-2-buten-1-ol to X-3 and X-2 (90:10:10) from gas chromatographic-mass spectral analyses of volatile extracts from male WTB feeding in branches of northern California black walnut, *J. hindsii*. The five treatments were replicated in three spatial blocks and the treatments were re-randomized among the five trap stations in a block each time the traps were emptied (nearly every day).

At the same time and location, the flight response of WTB to 3-methyl-2-buten-1-ol (release rate 15-80 mg/d LDPE plastic pouch, Contech) was tested in combination with each of the following compounds: DMNT [4,8-dimethyl-1,3(E),7-nonatriene], vittatol [(3R,6R)-3-hydroxy-2,2,6-trimethyltetrahydropyran], (−)- and (+)-rose oxide [tetrahydro-4-methyl-2-(2-methylpropenyl)-2H-pyran] (Table 3, Field Test 2). DMNT and vittatol were synthesized and provided by Prof. Wittko Francke, University of Hamburg, Institute of Organic Chemistry; whereas (−)-rose oxide (>99% chemical purity, product #83917-1 ML, Fluka, Milwaukee, Wis.) and (+)-rose oxide (>99% chemical purity, product #83915-1 ML, Fluka) were purchased. The compounds besides 3-methyl-2-buten-1-ol were released from closed 400 µl Eppendorf microcentrifuge tubes (Evergreen) with loads of approximately 50 µl (DMNT); 20 mg (vittatol, solid at room temperature); and approx. 200 µl each of (−)- and (+)-rose oxide. The six treatments were replicated in three spatial blocks and the treatments were re-randomized among the six trap stations in a block each time the traps were emptied (nearly every day).

Finally, a flight bioassay of the effect of the compound racemic trans-"pityol" [2-(1-hydroxy-1-methylethyl)-5-methyltetrahydrofuran] was conducted in late summer/early fall at Wolfskill Experimental Orchards. Pityol is a component of the aggregation pheromone of conifer-infesting *Pityophthorus* species. The response of WTB to racemic trans-pityol (formulated in a polyvinylchloride plastic bubble cap release device, 40 mg load, 0.2 mg/d release rate at 20° C., product #300000272, Contech Enterprises) and pityol in combination with 3-methyl-2-buten-1-ol (release rate 15-80 mg/d, LDPE plastic pouch Contech) was tested (Table 3, Field Test 3). The four treatments were replicated in three spatial blocks and the treatments were re-randomized among the four trap stations in a block each time the traps were emptied (nearly every day).

TABLE 3

Field bioassays of 3-methyl-2-buten-1-ol in combination with other compounds[a]

| Field Test 1, Winters, Solano Co., CA |
|---|
| X |
| X + X-3 |
| X + X-2 |
| X + X-3 + X-2 |
| Unbaited |
| Field Test 2, Winters, Solano Co., CA |
| X |
| X + dimethylnonatriene |
| X + vittatol |
| X + (−)-rose oxide |
| X + (+)-rose oxide |
| Unbaited |
| Field Test 3, Winters, Solano Co., CA |
| X |
| X + racemic trans-pityol |
| Racemic trans-pityol |
| Unbaited |

[a]X = 3-methyl-2-buten-1-ol; X-3 = 3-methyl-3-buten-1-ol; X-2 = 3-methyl-1-butanol. All tests used 4-unit Lindgren funnel traps with propylene glycol antifreeze in the trap cup.

The four treatments were replicated in three spatial blocks and the treatments were re-randomized among the four trap stations in a block each time the traps were emptied (nearly every day).

Statistical Analyses.

Analysis of treatment effects for the pouch vs. bottle experiment was done by using a sign test. (See Zar, J. H. 2010. Biostatistical Analysis. 5$^{th}$ ed. Pearson Prentice Hall, Englewood Cliffs, N.J.) The other four experiments were analyzed for treatment effect by using Friedman's non-parametric analysis of variance. Id. In all experiments, males and females were analyzed separately. All treatments within experiments yielding a significant treatment effect were compared by using an a posteriori Nemenyi test with experimentwise $\alpha=0.05$. Id. For all experiments, differences among proportions of female WTB responding to treatments were analyzed by comparing 95% confidence intervals determined with the Clopper-Pearson method. Id.

Results and Discussion

Field Testing of Various Release Rates of 3-methyl-2-buten-1-ol.

Total trap catch in the two release rate (pouch vs. bottle) experiment was 9,269 (3112 male/6157 female); catches to traps baited with 15-80 mg/d 3-methyl-2-buten-1-ol (pouch) were 1284 male/3085 female, and catches to traps baited with 5 mg/d 3-methyl-2-buten-1-ol (bottle with 15 ml load) were 1828 male/3072 female, N=40. A two-sided non-parametric sign test showed a significant difference between treatment for males (P≤0.02, N=38), but not for females (P≥0.2, N=37). In particular, the male response was greater for the lower release rate plastic bottle treatment. Proportions of females responding to the lower and higher release rate were 0.63 and 0.71, respectively, with overlapping Clopper-Pearson 95% confidence intervals (0.613-0.641 and 0.692-0.720, respectively).

Figure 5:
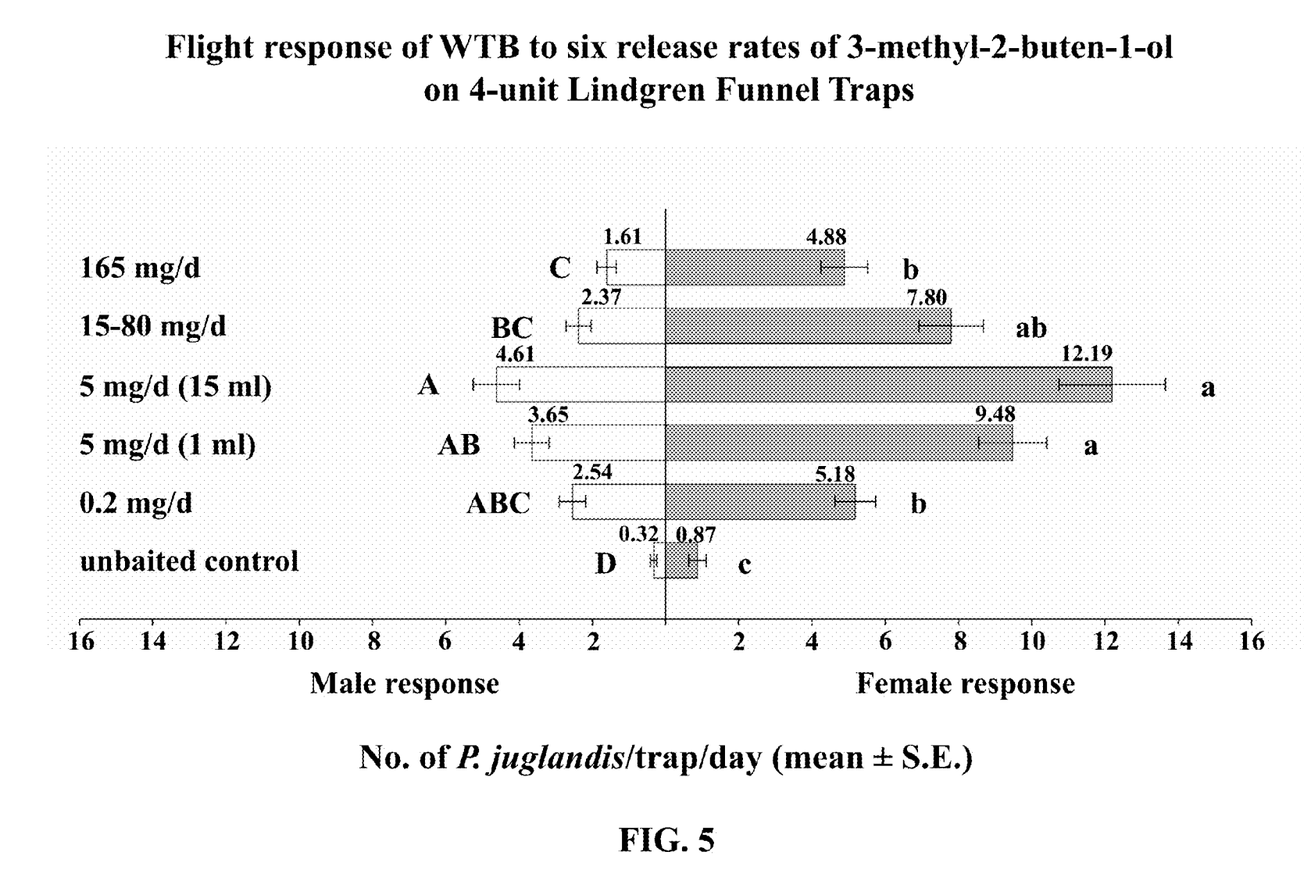
FIG. 5 shows the flight response of WTB to 4-unit Lindgren funnel traps baited with various release rates of 3-methyl-2-buten-1-ol.

The results of the six release rate experiment are shown in FIG. 5. Total trap catch in the six release rate experiment was 6,785 (1907 male/4878 female); catches to 165 mg/d (15 ml load) were 205 male/612 female, catches to 15-80 mg/d were 285 male/934 female; catches to 5 mg/d (15 ml load) were 608 male/1534 female; catches to 5 mg/d (1 ml load) were 453 male/1084 female; catches to 0.2 mg/d were 323 male/623 female; and catches to the unbaited trap were 33 male/91 female, N=99. Friedman's non-parametric analyses of variance showed significant treatment effects for males (P<0.001, N=97) and females (P<0.001, N=99). Nemenyi's multiple comparisons (experimentwise $\alpha=0.05$ within each sex) are shown on the histograms. The highest response for both sexes was to the 5 mg/d release loaded with 15 ml of pheromone. The impact of release rate on the flight response is further evidence for 3-methyl-2-buten-1-ol as a male-produced aggregation pheromone of WTB. Proportions of females responding to 165 mg/d, 15-80 mg/d, 5 mg/d (15 ml load), 5 mg/d (1 ml load), 0.2 mg/d, and 0 mg/d were 0.75, 0.77, 0.72, 0.71, 0.66, and 0.74, respectively, with non-overlapping Clopper-Pearson 95% confidence intervals (0.718-0.778, 0.741-0.790, 0.697-0.735, 0.682-0.728, 0.627-0.689, and 0.647-0.809, respectively).

Field Bioassays of 3-methyl-2-buten-1-ol in Combination with Other Compounds.

The results of Field Test 1 showed that the presence of X-3 and X-2 alone or in combination did not significantly affect the flight response of WTB to the aggregation pheromone, 3-methyl-2-buten-1-ol, at the release rates tested. Total trap catch in this experiment was 3,249 (709 male/2540 female); catches (male/female) to the unbaited traps were 14/12; to the traps baited with 15-60 mg/d 3-methyl-2-buten-1-ol were 193/636; to traps baited with 3-methyl-2-buten-1-ol and 3-methyl-3-buten-1-ol were 147/614; to traps baited with 3-methyl-2-buten-1-ol and 3-methyl-1-butanol were 145/578; and to traps baited with 3-methyl-2-buten-1-ol (X), 3-methyl-3-buten-1-ol (X-3), and 3-methyl-1-butanol (X-2) were 210/700, N=42. The total percentage female for all traps was 78.2%. Friedman's non-parametric analyses of variance showed significant treatment effects for males (P<0.001, N=38) and females (P<0.001, N=42). Nemenyi's multiple comparisons (experimentwise $\alpha=0.05$ within each sex) were obtained. Proportions of females responding to X, X+X-3, X+X-2, and X+X-3+X-2 were 0.77, 0.81, 0.80, and 0.77, respectively, with overlapping Clopper-Pearson 95% confidence intervals (0.737-0.796; 0.777-0.834; 0.768-0.828; and 0.710-0.796, respectively).

The results of Field Test 2 showed that none of the compounds significantly affected the response of WTB to 3-methyl-2-buten-1-ol, at the release rates tested. Total trap catch in this experiment was 763 (219 male/544 female); catches (male/female) to the unbaited traps were 2/3; to the traps baited with 15-60 mg/d compound X were 43/100; to traps baited with compound X and DMNT were 32/125; to traps baited with compound X and vittatol were 44/110; to traps baited with compound X and (−)-rose oxide were 38/106; and to traps baited with compound X and (+)-rose oxide were 60/100, N=42. The total percentage female for all traps was 71.3%. Friedman's non-parametric analyses of variance showed significant treatment effects for males (P<0.001, N=38) and females (P<0.0001, N=42). Nemenyi multiple comparisons (experimentwise $\alpha=0.05$ within each sex) were obtained. Proportions of females responding to unbaited, X, X+DMNT, X+vittatol, X+(−)-rose oxide, X+(+)-rose oxide were 0.6, 0.70, 0.80, 0.71, 0.74, and 0.63, respectively, with 95% confidence intervals 0.15-0.95; 0.617-0.773; 0.725-0.856; 0.636-0.784, 0.656-0.806; and 0.545-0.700, respectively.

The results of Field Test 3 showed that the presence of pityol did not significantly affect the response to 3-methyl-2-buten-1-ol at the release rates tested. Total trap catch in this experiment was 4,491 (976 male/3515 females); catches (male/female) to the unbaited traps were 42/36; to traps baited with 15-80 mg/d 3-methyl-2-buten-1-ol were 539/2100; to traps baited with pityol were 32/11; and to traps baited with the combination of compound X and pityol were 363/1368, N=93. The total percentage female response for all traps was 78.3%. Friedman's non-parametric analyses of variance showed significant treatment effects for males (P<0.001, N=70) and females (P<0.001, N=90). Nemenyi multiple comparisons (experimentwise $\alpha=0.05$ within each sex) were obtained. Proportions of females responding to unbaited, X, pityol, and X+pityol were 0.47, 0.80, 0.24, 0.79, respectively, with 95% confidence intervals 0.36-0.58; 0.779-0.810; 0.13-0.39; and 0.766-0.804, respectively.

Example 3

Selection of Trap Type and Trap Height

Methods and Materials

Selection of Trap Type.

The flight response of WTB to various trap types was tested at several sites in northern California. In one set of experiments, the response to yellow sticky card traps and 4-unit Lindgren funnel traps was tested. Both traps were baited with male+female-WTB-infested branches of *J. hindsii*, which constituted a natural source of aggregation pheromone. Both traps were placed at about 2 m height. The experiment was conducted in early spring in Davis, Yolo Co., Calif. Two replicates of each trap type were in place for the study and the treatments were re-randomized among the trap stations each time that the traps were emptied (weekly). Trap catches of males and females were normalized by the available trapping surface area for each trap type.

In another set of experiments, the response of WTB to clear sticky panel traps and 4-unit Lindgren funnel traps was tested. Both were baited with 3-methyl-2-buten-1-ol (5 mg/d, 15 ml load). The clear plexiglass panel traps were coated with Stikem Special (Seabright Labs, Emeryville, Calif.). The experiment was conducted in late spring in a native riparian stand of *J. hindsii* at Shadow Cliffs Regional Park, Alameda Co., Calif. The pairs of traps were hung at a height of 3 m in the crowns of *J. hindsii* and arranged in six spatial blocks. Treatments were re-randomized among the trap stations each time that the traps were emptied (approx. weekly, after periodic WTB flights). Trap catches of males and females were normalized by the available trapping surface area for each trap type.

In another set of experiments, the flight response of WTB to four types of Lindgren funnel traps (Contech) and an intercept panel trap (Alpha Scents Inc., Portland Oreg., product # AST0031) was tested at Wolfskill Experimental Orchards in mid-summer. Each trap was baited with the commercial formulation of 3-methyl-2-buten-1-ol (15-80 mg/d, Contech) hung inside the middle funnel of each funnel trap or in a recess in the middle of the cross vane panels of the panel trap. Each trap cup was filled with propylene glycol as described above and the traps were suspended from the top of a 3 m metal conduit pole. Three blocks of traps were installed and trap catches were collected daily when the flight activity was high. The five treatments were re-randomized among the five trap stations within each of the three blocks each time that the traps were emptied.

Effect of Trap Height on Trap Catch.

The flight response of WTB to clear plexiglass panel traps coated with Stikem Special (Seabright Labs, Emeryville, Calif.) and baited with 3-methyl-2-buten-1-ol (5 mg/d, 15 ml load, polyethylene bottle) located at three heights (2, 3, and 4 m above the forest floor) was tested. The traps were placed in the crowns of *J. hindsii* located in a native riparian stand at Shadow Cliffs Regional Park, Alameda Co., Calif. from early to mid-spring. Both sides of a single 23 cm×14 cm sheet of clear plexiglass were covered with Stikem Special adhesive and the sheet was hung from string at each of the 3 heights from a single *J. hindsii* branch. The aggregation pheromone bait was hung immediately above each trap. Each group of three traps was assigned a unique position within the stand and treated as a block in a completely randomized block design (N=22). Traps within a block were all collected on the same day; blocks were collected after 2 to 7 days (after periodic flights of WTB).

In another experiment, the effect of trap height on the flight response of WTB was also tested with 4-unit Lindgren funnel traps at Wolfskill Experimental Orchards from late summer to early fall. The traps were each baited with the commercial version of 3-methyl-2-buten-1-ol (15 to 80 mg/d, Contech pouch) and placed at 45, 123, 199, and 271 cm (hereafter 0.5, 1.2, 2.0, and 2.7 m) from the orchard floor (measured from the floor to the middle of the trap). Traps were attached to individual 3 m metal conduit poles by using a thick piece of wire threaded through a hole drilled in the conduit pole and the eyebolt attached to the top of the funnel trap. (See Seybold, S. J., Dallara, P. L., Hishinuma, S. M., and Flint, M. L. Detecting and Identifying the Walnut Twig Beetle: Monitoring Guidelines for the Invasive Vector of Thousand Cankers Disease of Walnut, University of California Agriculture and Natural Resources, Statewide Integrated Pest Management Program, 11 pp., Apr. 30, 2012.) Three blocks of treatments were installed, trap catches were collected daily during periods of high flight activity, and the treatments were re-randomized among the four trap stations within a block each time that the traps were emptied.

Effects of Miscellaneous Manipulations on Trap Catches.

To evaluate increased efficacy of the 4-unit Lindgren funnel trap, the effect of Rain•X (SOPUS Products, Houston, Tex.), a glass surfactant shown to increase the trap catches of other beetles when sprayed onto funnel traps and buffed with a microfiber towel, was tested. (See Francese, J. A., Fraser, I., Lance, D. R., and Mastro, V. C. 2011. Efficacy of multifunnel traps for capturing emerald ash borer (Coleoptera: Buprestidae): Effect of color, glue, and other trap coatings. *Journal of Economic Entomology* 104: 901-908.) Four pairs of funnel traps (both baited with 3-methyl-2-buten-1-ol, 15-80 mg/d, Contech) were placed at Wolfskill Experimental Orchards in early summer. One trap from each pair was sprayed with Rain•X and buffed with a microfiber towel. This application was repeated and then the treated and untreated traps were grouped into 4 blocks. Traps were emptied twice each day, and the treatments were re-randomized among the two trap stations in each block during the morning emptying period (generally 6 to 7 AM). (See Seybold, S. J. King, J. A., Harris, D. R., Nelson, L. J., Hamud, S. M., and Chen, Y. Diurnal flight response of the walnut twig beetle, *Pityophthorus juglandis*, to pheromone-baited traps in two northern California walnut habitats. *Pan-Pacific Entomol.*, accepted in press June 2012.)

Statistical Analyses.

Analyses of treatment effects for the tests of trap type were performed by using Friedman's non-parametric analysis of variance or a sign test, depending on the number of treatments. (See Zar, J. H. 2010. Biostatistical Analysis. $5^{th}$ ed. Pearson Prentice Hall, Englewood Cliffs, N.J.) Analysis of treatment effects for the Rain•X experiment was performed by using a Wilcoxon paired sample test. Id. Multiple comparisons for experiments with more than two treatments were performed with an a posteriori Nemenyi test with experiment-wise $\alpha=0.05$. Id. In all cases, male and female WTB were analyzed separately. Proportions of female WTB responding to treatments were calculated and 95% confidence intervals determined by using the Clopper-Pearson method. Id.

Results and Discussion

Selection of Trap Type.

Figure 6:
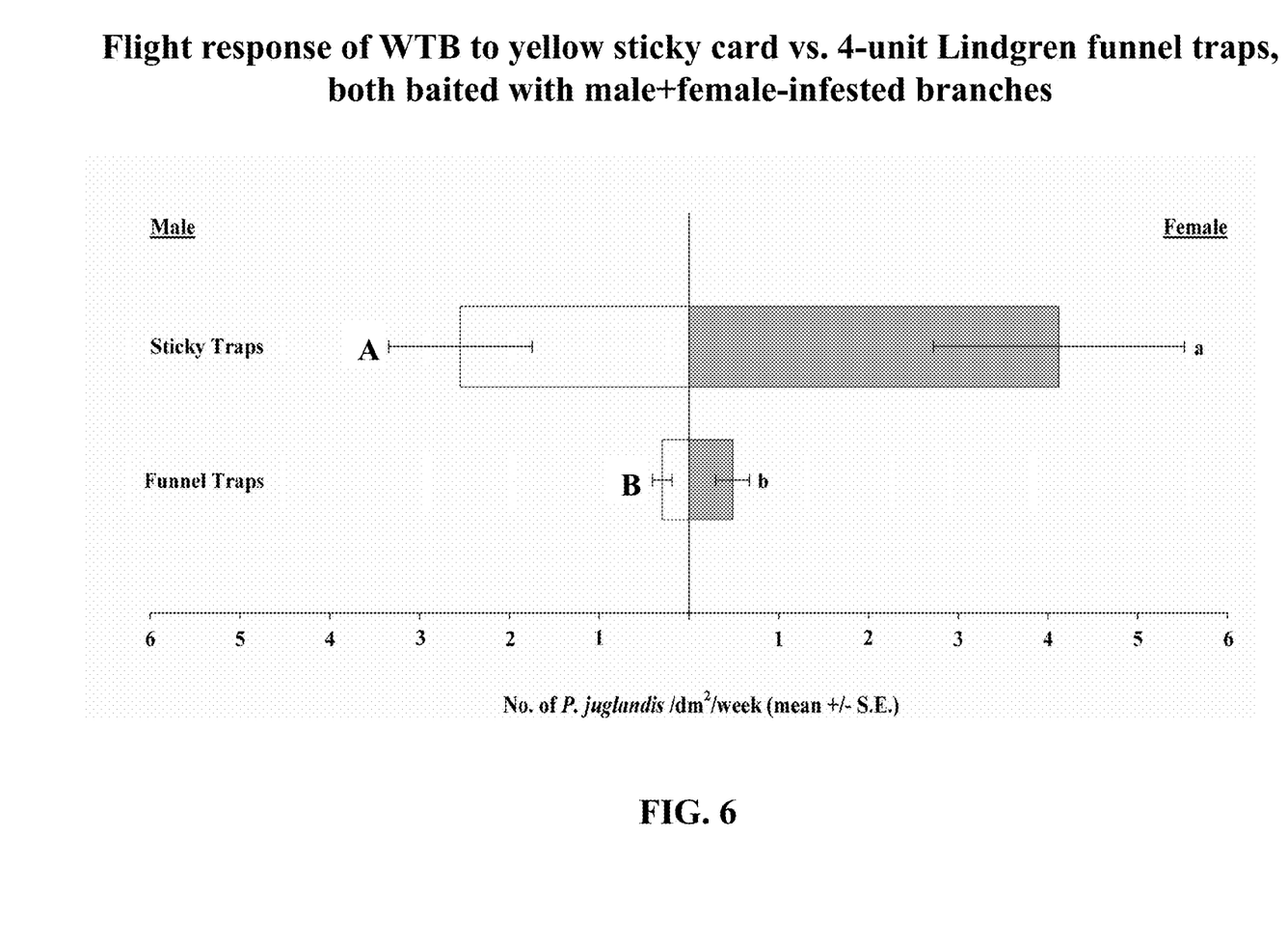
FIG. 6 shows the flight response of WTB to yellow sticky card or 4-unit Lindgren funnel traps baited with male and female WTB-infested branches of *J. hindsii*, a natural blend of potential semiochemicals including the pheromone component 3-methyl-2-buten-1-ol.

As described above, the flight response of WTB to yellow sticky card vs. 4-unit Lindgren funnel traps, both baited with male+female-infested branches was recorded. The results are shown in FIG. 6. Following a normalization of the trap catches based on the surface area of each trap type, the analysis revealed that the sticky traps caught significantly more WTB of either sex than the funnel traps (males: $P=0.002$ N=44, females: $P=0.02$, N=47, sign test). Total trap catch in this experiment was 1,228 (487 male/741 female), 60.3% female. Total trap catch was 825 on the yellow sticky cards and 403 in the 4-unit funnel traps. Proportions of females responding to yellow sticky and funnel traps were 0.58 and 0.62, respectively, with overlapping 95% Clopper-Pearson confidence intervals (0.528-0.627 and 0.582-0.649, respectively).

As described above, the flight response of WTB to clear sticky panel traps and 4-unit Lindgren funnel traps, both baited with 3-methyl-2-buten-1-ol (5 mg/d, 15 ml load) was also recorded. As in the previous experiment, sticky traps caught significantly more WTB than funnel traps when normalized for surface area. Total trap catch was 935 (326 males/609 females), 65.1% female; for sticky panels the catch was 216 males/449 females, for funnel traps, 110 males/160 females. Treatment within sex had a significant effect (males $P<0.001$ N=24: females $P<0.001$, N=24, 2-sided sign test).

Proportions of females responding to sticky and funnel traps were 0.67 and 0.59 respectively, with overlapping 95% Clopper-Pearson confidence intervals (0.639-0.710 and 0.531-0.652, respectively.

As described above, flight responses of WTB to four types of Lindgren funnel traps (Contech) and an intercept panel trap were also recorded. The 12-unit funnel trap caught the most WTB. However, when normalized for the available trapping surface area, there were no differences in trap catches among the funnel traps. Total trap catch in this experiment was 3,658 (987 male/2671 female); catches in the 4-unit Lindgren funnel trap were 72 male/231 female, catches in the 8-unit trap were 202 male/634 female; catches in the 12-unit trap were 352 male/892 female; catches in 16-unit trap were 233 male/618 female; and catches in the intercept panel trap were 128 male/296 female. Friedman's non-parametric analyses of variance showed significant treatment effects for males ($P<0.001$, $N=33$) and females ($P<0.001$, $N=34$). Proportions of females responding to the 4-unit, 8-unit, 12-unit, 16-unit, and panel trap were 0.76, 0.76, 0.72, 0.73, and 0.70, respectively, with overlapping Clopper-Pearson 95% confidence intervals (0.714-0.810, 0.729-0.787, 0.692-0.742, 0.696-0.756, and 0.654-0.742, respectively).

Effect of Trap Height on Trap Catch.

As described above, the flight response of WTB to clear plexiglass panel traps coated with Stikem Special and baited with the WTB aggregation pheromone (5 mg/d, 15 ml load) located at three heights (2, 3, and 4 m above the forest floor) was tested. Total trap catch was 1,088 (342 male/746 female), 69% female. Friedman's non-parametric analyses of variance showed a significant treatment effect for females $X^2=12.1$, $P=0.002$, $N=22$) but not for males ($X^2=4.1$, $P=0.126$; $N=22$). Female WTB showed a significantly higher response to baited plexiglass traps 4 m from the ground as compared to 3 or 2 m. Proportions of females responding to the 2, 3, and 4 m traps were 0.68, 0.64, and 0.72, respectively, with overlapping Clopper-Pearson 95% confidence intervals (0.631-0.737, 0.586-0.691, and 0.678-0.759, respectively).

As described above, the effect of trap height on the flight response of WTB was also tested with 4-unit Lindgren funnel traps. Total trap catch in this experiment was 3,247 (754 male/2493 female); catches in the 2.7 m trap were 225 male/757 female, catches in the 2.0 m trap were 265 male/875 female; catches in the 1.2 m trap were 139 male/469 female; and catches in the 0.5 m trap were 125 male/392 female. Friedman's non-parametric analyses of variance showed significant treatment effects for males ($P<0.001$, $N=74$) and females ($P<0.001$, $N=83$). Nemenyi's multiple comparisons (experimentwise $\alpha=0.05$ within each sex) were obtained. Traps at 2 m and 2.7 m caught the most WTB. Proportions of females responding to the 2.7 m, 2.0 m, 1.2 m, and 0.5 m traps were 0.77, 0.77, 0.77, and 0.76, respectively, with overlapping Clopper-Pearson 95% confidence intervals (0.743-0.797, 0.742-0.792, 0.736-0.804, and 0.719-0.795, respectively).

Effects of Miscellaneous Manipulations on Trap Catches.

As described above, the effect of Rain•X treatment on WTB flight response to 4-unit Lindgren funnel traps was tested. Total trap catch was 6,573 (1093 male/5480 female), 83.4% female. There was no significant difference for either sex (males: $T=978$, $P>0.5$, $N=63$; females: $T=1157$, $P>0.5$, $N=69$, Wilcoxon paired sample test). Proportions of females responding to the Rain•X and control treatments were 0.84 and 0.83, respectively, with overlapping Clopper-Pearson 95% confidence intervals (0.824-0.848 and 0.816-0.844, respectively).

Example 4

Testing WTB Field Detection Methods in Idaho, Utah, Tennessee, and Virginia

Methods and Materials

The efficacy of the WTB trap bait as a detection tool was tested across the United States for a range of populations of the beetle that might be biologically heterogeneous and may occur at various densities in the landscape. The information learned from these trials was instrumental in preparing the national trapping guidelines for walnut twig beetle. (See Seybold, S. J., Dallara, P. L., Hishinuma, S. M., and Flint, M. L. Detecting and Identifying the Walnut Twig Beetle: Monitoring Guidelines for the Invasive Vector of Thousand Cankers Disease of Walnut, University of California Agriculture and Natural Resources, Statewide Integrated Pest Management Program, 11 pp., Apr. 30, 2012; Seybold, S. J., Dallara, P. L., Hishinuma, S. M., and Flint, M. L. Quick guide: Installing, maintaining, and servicing walnut twig beetle pheromone-baited traps, University of California Agriculture and Natural Resources, Statewide Integrated Pest Management Program, 2 pp., April 2012.) Throughout the summer months, separate experiments were initiated in Idaho and Utah, around Knoxville, Tenn., and around Richmond, Va. For each state, trapping was performed in areas of known WTB infestation as well as nearby localities where WTB had not been previously detected. In Idaho and Utah, trapping was conducted from the months of June through November and reinitiated in March of the following year. In Tennessee, trapping was conducted from July through mid-December; carried out on a reduced scale from December through April of the following year; and then reinitiated in full in April. In Virginia, trapping was conducted from August through mid-December; carried out on a reduced scale from December through April of the following year; and then reinitiated in full in April.

In Idaho, Utah, and Tennessee, WTB were trapped with 4-unit Lindgren funnel traps; in Virginia, 12-unit traps were used. Traps were baited with 3-methyl-2-buten-1-ol (15-80 mg/d, Contech). Approximately 150 ml of a propylene glycol-water solution (recreational vehicle/marine antifreeze) was placed in each trap collection cup to immobilize and preserve trapped insects. Each trap was hung from the top of a 10 ft (3 m)×0.5 in (1.27 cm) electrical conduit (EMT) pole and emptied every 2 weeks. Traps were placed near individual or small groups of eastern black walnut, *Juglens nigra*; in Idaho and Utah several traps were placed near Persian walnut, *J. regia*.

Traps in the Utah study (N=22) were positioned along a north-south transect that included sites in Cache, Box Elder, Weber, Davis, Salt Lake, and Utah Counties, as well as Franklin Co., Idaho; the survey was extended to the south to include traps in Iron Co. Transect length was approximately 500 km. The survey points in Idaho (N=20) were positioned in an approximate north-south transect that crossed Boundary, Bonner, Kootenai, Clearwater, Nez Perce, Gem, Ada, and Canyon Counties, spanning approximately 600 km. In Tennessee, traps (N=17) were placed in Knox County (near the site of the state's first WTB detection) and in twelve additional surrounding counties: Loudon, Blount, Monroe, Claibourne, Sevier, Jefferson, Campbell, Grainger, Morgan, Roane, Scott, and Cocke. In Virginia, traps (N=18) were deployed in Richmond City (near the site of Virginia's first WTB detection) and in ten surrounding counties: Chesterfield, Henrico, Goochland, Powhatan, Charles City, Dinwiddie, Louisa, Hanover, Amelia, and King William.

To compare the effectiveness of the bait in the eastern range of WTB, pairs of baited and unbaited traps were located in Tennessee (3 pairs, 10 repeated measures for each pair) and Virginia (4 pairs, 12 repeated measures for each pair). The traps in each pair were placed approximately 15 m apart on opposite sides of the same tree (*J. nigra*) at each site. Trap catch data were analyzed with a sign test. In other experiments, these pairs of traps were re-installed at some of the same locations in Tennessee and Virginia and more pairs were added for the first time in Pennsylvania and Utah.

Results and Discussion

The demonstration trials in the four states resulted in the capture of 15,693 WTB from a time period extending from early summer to mid-fall. The Utah transect yielded 3,996 WTB during this time period, with positive trap catches in all tested counties except Franklin in Idaho. In the following spring, WTB were also found at the two added sites in Iron Co. WTB were detected in traps near *J. nigra* as well as *J. regia*. In Idaho, a total of 7,155 WTB were detected during a time period extending from mid-summer to early fall in all counties except Bonner and Boundary, the northernmost portion of this transect. Tennessee traps yielded 1,254 WTB during a time period extending from mid-summer to mid-fall in eight of the thirteen counties tested. Virginia traps yielded 3,288 WTB during a time period extending from late summer to early fall in Richmond City and five counties: Chesterfield, Henrico, Goochland, Powatan, and Hanover.

Although WTB were detected during each month of trapping in each state, trap catches peaked in Utah, Tennessee, and Virginia during July and August; peak trap catches for Idaho were observed in August and September. Traps in Utah and Idaho were removed in the months of October and November, respectively, and redeployed in March of the following year. A subset of the traps in Tennessee and Virginia remained in place during the winter and continued to yield WTB during each month from January to April of the following year in both states.

Figure 7:
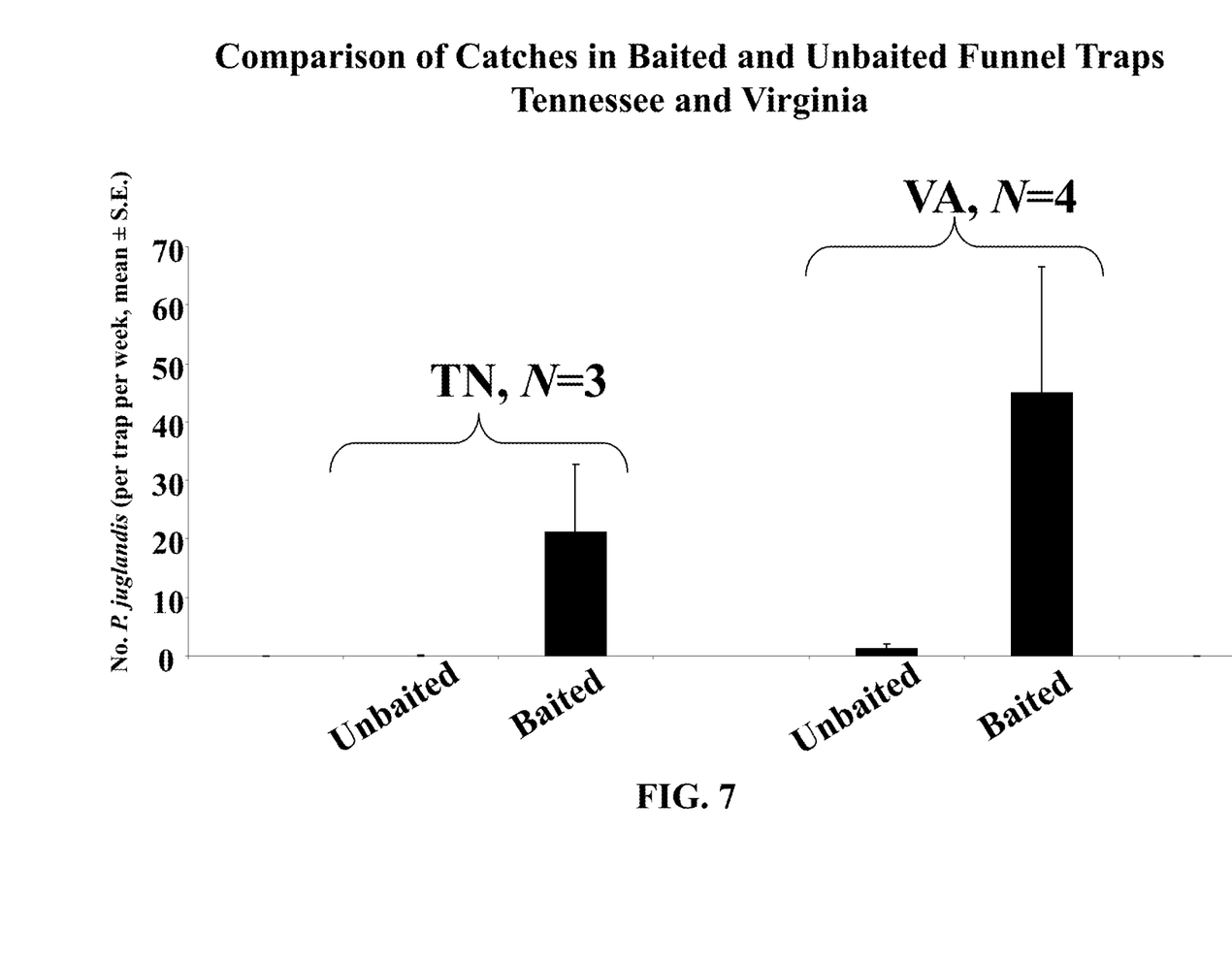
FIG. 7 shows the WTB flight response to baited (with 3-methyl-2-buten-1-ol) and unbaited Lindgren funnel trap pairs around Knoxville, Tenn. (N=30) and Richmond, Va. (N=48).

As shown in FIG. 7, catches of WTB at baited traps were significantly greater than those at unbaited traps. In Tennessee, 19.1 WTB/trap/week were detected at baited traps, whereas 0.1 WTB/trap/week were found at unbaited traps. In Virginia, 42.3 WTB/trap/week were captured in baited traps, whereas 1.3 WTB/trap/week were captured in unbaited traps. Both results were significantly different for each sex ($P<0.001$, 2-sided sign test, N=30 in TN and N=48 in VA).

The results show that the detection of WTB with pheromone-baited traps can serve as an early detection system for thousand cankers disease (TCD). Prior to these demonstration trials, visual and sampling surveys for symptoms of TCD on walnut trees were conducted in Tennessee and Virginia by state agricultural agencies. Among other counties in Tennessee, no symptoms of TCD were found in Grainger, Campbell, Jefferson, or Cocke Counties. However, as described above, WTB was detected in all four of these counties, resulting in these counties being subsequently surveyed more intensively for TCD. Similarly, WTB were found in four areas of Virginia that had yielded no trees symptomatic for TCD. Subsequent surveys positively identified TCD in *J. nigra* located near the WTB detection traps.

Finally, these results also suggest that populations of WTB that are widely separated geographically respond similarly to the WTB pheromone. This is further corroborated by preliminary results of WTB trapping efforts in Pennsylvania. Thus, the utility of the aggregation pheromone as a national detection tool has been demonstrated. As a consequence of these trials outside of California, new limits of the range of WTB in the United States have been established. (See Seybold, S. J., Coleman, T. W., Dallara, P. L., Dart, N. L., Graves, A. D., Pederson, L., and Spichiger, S.-E. 2012a. Recent collecting reveals new state records and the extremes in the distribution of the walnut twig beetle, *Pityophthorus juglandis* Blackman (Coleoptera: Scolytidae), in the United States. *Pan-Pacific Entomol.* (accepted, in press May 30, 2012).

The word "illustrative" or "exemplary" is used herein to mean serving as an example, instance, or illustration. Any aspect or design described herein as "illustrative" or "exemplary" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like includes the number recited and refers to ranges which can be subsequently broken down into subranges as discussed above. Finally, as will be understood by one skilled in the art, a range includes each individual member.

The foregoing description of illustrative embodiments of the invention have been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A system comprising:
    an effective amount of a composition, the composition comprising a semiochemical capable of being produced by *Pityophthorus juglandis*, and
    a permeable container or a support substrate holding the composition and configured to release the semiochemical over a period of time at a release rate,
    wherein the system is configured for use in the treatment of a surface subject to infestation by *Pityophthorus juglandis*, and further wherein the semiochemical is 3-methyl-2-buten-1-ol and the release rate is in the range of from about 0.2 µg/day to about 200 mg/day.

2. The system of claim 1, wherein the system further comprises another composition comprising a racemic mixture of trans-(5S,7S)-7-methyl-1,6-dioxaspiro[4,5]decane, (−)-trans-(5S,7S)-7-methyl-1,6-dioxaspiro[4,5]decane, a racemic mixture of 2-ethyl-1,6,-dioxaspiro[4,4]nonane, or combinations thereof.

3. The system of claim 1, comprising the permeable container.

4. The system of claim 3, wherein the permeable container is a pouch or a bubble cap.

5. The system of claim 1, further comprising a trap coupled to the composition, the trap configured to capture *Pityophthorus juglandis*.

6. The system of claim 1, wherein the release rate is in the range of from about 0.1 mg/day to about 150 mg/day.

7. A system for treating a surface subject to infestation by *Pityophthorus juglandis*, the system comprising:
   a composition comprising a semiochemical capable of being produced by *Pityophthorus juglandis*; and
   an insect trap comprising a bait;
   wherein the semiochemical is 3-methyl-2-buten-1-ol and the bait for the insect trap is the composition; and further wherein the system is configured to release the semiochemical over a period of time at a release rate in the range of from about 0.2 µg/day to about 200 mg/day.

8. The system of claim 7, further comprising a release device holding the composition and configured to release the semiochemical over the period of time at the release rate.

9. The system of claim 7, wherein the release rate is in the range of from about 0.1 mg/day to about 150 mg/day.

* * * * *